United States Patent [19]

Fujii et al.

[11] Patent Number: 4,777,182
[45] Date of Patent: Oct. 11, 1988

[54] 6-AMIDINO-2-NAPHTHYL 4-GUANIDINOBENZOATE DERIVATIVES AND PHARMACEUTICAL COMPOSITION CONTAINING THEM

[75] Inventors: Setsurou Fujii, Kyoto; Toshiyuki Okutome, Tokyo; Toyoo Nakayama, Funabashi; Shigeki Nunomura; Kimio Sudo, both of Chiba; Shinichi Watanabe, Otsu; Masateru Kurumi, Narita; Takuo Aoyama, Sakura, all of Japan

[73] Assignee: Torii & Co., Ltd., Tokyo, Japan

[21] Appl. No.: 835,853

[22] PCT Filed: Jul. 12, 1985

[86] PCT No.: PCT/JP85/00392

§ 371 Date: Feb. 24, 1986

§ 102(e) Date: Feb. 24, 1986

[87] PCT Pub. No.: WO86/00893

PCT Pub. Date: Feb. 13, 1986

[30] Foreign Application Priority Data

Jul. 25, 1984 [JP] Japan ............... 59-155045

[51] Int. Cl.$^4$ ............... A61K 31/415; A61K 31/505; C07D 233/50; C07D 233/88
[52] U.S. Cl. ................... 514/392; 514/218; 514/256; 514/275; 514/535; 540/553; 544/332; 548/315; 560/34
[58] Field of Search ............ 544/332; 548/315; 540/553; 564/238; 560/34; 514/218, 256, 275, 392, 535

[56] References Cited

U.S. PATENT DOCUMENTS

| 4,420,619 | 12/1983 | Marxer | 548/315 |
| 4,454,338 | 6/1984 | Fujii et al. | 560/12 |
| 4,532,255 | 7/1985 | Fujii et al. | 514/466 |
| 4,598,077 | 7/1986 | Fujii et al. | 560/34 |

OTHER PUBLICATIONS

Webster's New Int'l Dictionary, Second Edition, (1961), p. 562, "Congestion".
Dorland's Illustrated Medical Dictionary, Twenty-Sixth Edition, (1981), p. 298, "Congestion".
Animal and Clinical Pharmacologic Techniques in Drug Evaluation, Edited by Nodine & Siegler, Chapter 7.
"Stages of Drug Evaluation in Man; General Principals of Experimental Design", by John H. Nodine, M.D., pp. 89–95, esp. p. 90, published 1964, Yearbook Medical Publishers, Inc., Chicago.

Primary Examiner—Mary C. Lee
Assistant Examiner—Kurt G. Briscoe
Attorney, Agent, or Firm—Beveridge, DeGrandi & Weilacher

[57] ABSTRACT

Amidine compounds of formula (I)

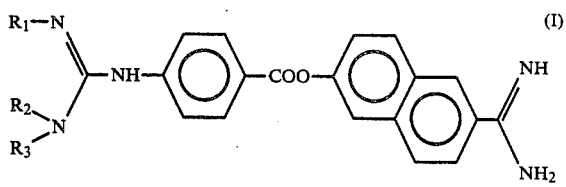

and the pharmaceutically acceptable acid addition salts thereof are novel and are of use as anti-trypsin, anti-plasmin, anti-kallikrein, anti-thrombin and anti-complement agents which may be administered orally. These amidine compounds can be produced by the reaction between a carboxylic acid compound of formula (II)

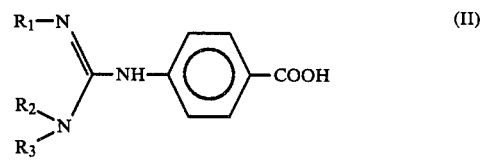

or a reactive intermediate thereof and 6-amidino-2-naphthol of formula (III)

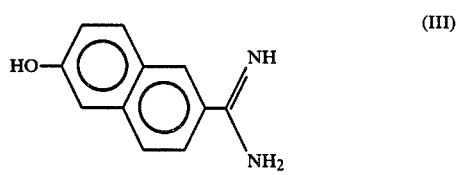

or preferably an acid addition salt thereof.

18 Claims, No Drawings

6-AMIDINO-2-NAPHTHYL 4-GUANIDINOBENZOATE DERIVATIVES AND PHARMACEUTICAL COMPOSITION CONTAINING THEM

FIELD OF THE ART

The present invention relates to amidine compounds having anti-trypsin, anti-plasmin, anti-kallikrein, anti-thrombin and anti-complement activities.

BACKGROUND OF THE ART

Compounds having anti-trypsin, anti-plasmin, anti-kallikrein, anti-thrombin and anti-complement activities have already been known from British Pat. No. 2,083,818.

The present compounds are stronger in enzyme inhibitory activities and anti-complement activity, and more effective in oral administration than the above prior compounds.

DISCLOSURE OF THE INVENTION

The present invention relates to novel amidine compounds of formula (I)

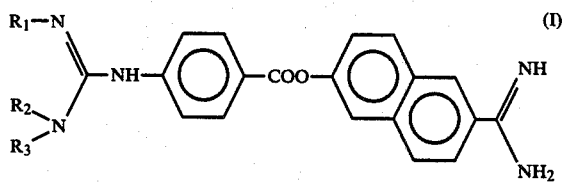

wherein $R_1$ and $R_2$ represent each a hydrogen atom, or a straight or branched chain alkyl group of 1 to 6 carbon atoms; $R_3$ represents a straight or branched chain alkyl group of 1 to 6 carbon atoms, or a group of the formula $R_4$—B—$(CH_2)_n$— wherein n is 1 to 2, B is —O— or —NH— and $R_4$ is a hydrogen atom, $R_5$—CO— or

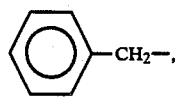

$R_5$ is a straight or branched chain alkyl group of 1 to 15 carbon atoms; and $R_1$ and $R_3$ taken together via 2 to 4 carbon atoms may form a ring optionally containing double bonds and straight or branched chain alkyl groups of 1 to 4 carbon atoms as substituents, and the pharmaceutically acceptable acid addition salts thereof.

An object of the present invention is to provide pharmaceutically useful novel amidine compounds and pharmaceutically acceptable acid addition salts thereof.

Another object of the present invention is to provide a process for producing said novel amidine compounds.

A still another object of the present invention is to provide anti-trypsin, anti-plasmin, anti-kallikrein, anti-thrombin and anti-complement agents which may be administered orally.

The compound (I) of the present invention can be produced by the reaction between a carboxylic acid compound of formula (II) or a reactive intermediate thereof and 6-amidino-2-naphthol of formula (III) or preferably an acid addition salt thereof.

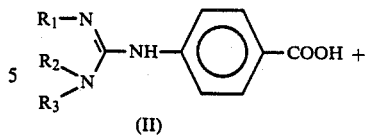

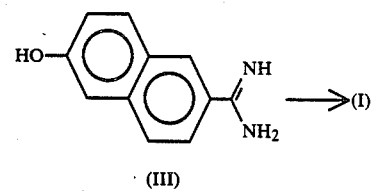

$R_1$, $R_2$ and $R_3$ are as defined above. The reactive intermediates, as herein referred to, include acid halides and acid anhydrides commonly used in the dehydration condensation and the reactive intermediates formed by reacting dicyclohexylcarbodiimide (DCC), diphenyl phosphorylazide (DPPA), or the like with a carboxylic acid derivative.

The process for producing the present compound is described below in detail.

The present compound (I) can be prepared by dissolving or suspending a carboxylic acid compound (II) in an organic solvent such as dimethylformamide, pyridine, or the like, then allowing the compound (II) to react with a carboxylic acid activator such as dicyclohexylcarbodiimide (DCC), diphenylphosphoryl azide (DPPA), or the like, which is usually used as dehydration-condensation agent, and adding 6-amidino-2-naphthol (III) or preferably an acid addition salt thereof to the reaction product.

For instance, when DCC is used as the dehydration-condensation agent, a carboxylic acid derivative (II) is added to a solvent such as pyridine, then 6-amidino-2-naphthol (III) is added, and the mixture is stirred at a temperature between −30° and 80° C., preferably at room temperature, for 3 to 5 hours to complete the reaction, though it is not objectionable to continue the reaction overnight. Dicyclohexylurea (DCU) precipitates out of the reaction mixture, while the present compound (I) either precipitates with DCU or remains dissolved in the solvent. In the former case, both precipitates are collected by filtration, then suspended in a suitable solvent such as dimethylformamide or the like and the mixture is filtered to remove insoluble DCU. After adding to the filtrate a solvent such as ethyl ether, ethyl acetate, acetone or the like, the precipitate is collected by filtration to obtain the present compound (I). Alternatively, the combined precipitate of DCU and the present compound (I) is collected by filtration, then added to a suitable solvent such as dimethylformamide, water or the like to remove insoluble DCU by filtration, the filtrate is added to a saturated aqueous sodium hydrogencarbonate solution to obtain the present compound (I) in the form of carbonate. In the latter case, where the present compound remains dissolved in the reaction mixture, DCU is removed by filtration and the filtrate is admixed with a solvent such as ethyl ether, acetone, ethyl acetate, or the like to obtain the present compound (I).

In another process, when it is intended to use an acid halide as a reactive intermediate of a carboxylic acid derivative (II), the latter derivative (II) is allowed to react with an acid halogenation agent such as $SOCl_2$, SOBr₂, PCl₅ or the like to synthesize an acid halide represented by formula (IV)

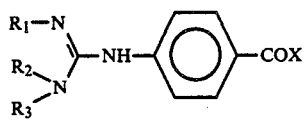

wherein $R_1$, $R_2$ and $R_3$ are as defined above and X represents a halogen atom. The acid halide is added to a solution of 6-amidino-2-naphthol (III), preferably in the form of an acid addition salt, dissolved in dimethylformamide, pyridine, dimethyl sulfoxide or the like and allowed to react in the presence of a dehydrohalogenation agent. The dehydrohalogenation agents which can be used include inorganic bases such as potassium carbonate, sodium carbonate, sodium hydroxide and the like and organic bases such as triethylamine, pyridine, dimethylaniline and the like. Of these bases, pyridine is preferred. Although the reaction proceeds readily at a temperature in the range of −30° to 80° C., it is preferable for the purpose of avoiding side reaction to conduct the reaction in the early stage under ice cooling and then at room temperature. The reaction is complete in 2 to 5 hours, though the reaction mixture can be left overnight. After completion of the reaction, the reaction mixture is treated in a customary manner. For instance, when pyridine was used as the reaction medium, a solvent such as ethyl ether or ethyl acetate is added to the reaction mixture to precipitate a solid reaction product which is then recrystallized from a suitable solvent such as a methanol-ethyl ether mixture to obtain the present compound (I).

The compound (III) is replaced by the corresponding compound wherein an amidino group is protected, and the latter compound can be allowed to react with the compound (II) to obtain the compound (I) wherein the amidino group is protected. Splitting off an amidino protecting group by a usual manner can yield the present compound (I).

The amidino protecting group may be conventionally used ones. Examples thereof include a benzyloxycarbonyl or t-butoxycarbonyl group. Examples of a method for splitting off an amidino protecting group include a reductive elimination by palladium-carbon or an elimination by trifluoroacetic acid or HBr/acetic acid.

If necessary, acid addition salts of the present compound may be prepared in a customary manner. For instance, carbonate of the present compound is dissolved or suspended in a solvent such as methanol, DMF or the like and the carbonate is allowed to dissolve by the addition of an acid such as methanesulfonic acid, hydrochloric acid or the like. To the resulting solution is added a solvent such as ethyl ether, ethyl acetate or the like to obtain a corresponding acid addition salt. Acids which can be used as pharmaceutically acceptable ones including inorganic acids such as hydrochloric acid, sulfuric acid and phosphoric acid and organic acids such as acetic acid, lactic acid, citric acid, methanesulfonic acid, succinic acid, fumaric acid and maleic acid.

The present compound and the pharmaceutically acceptable acid addition salt thereof possess powerful inhibitory activities against proteases, that is, trypsin, plasmin, kallikrein and thrombin and are effective as an anti-trypsin agent for the treatment of pancreatitis, as an anti-plasmin or anti-kallikrein agent for hemorrhagic diseases, and as an anti-thrombin agent for thrombus.

The present compound is easily absorbable and hence is effective not only when injected but also when used orally or as a suppository.

With respect to the above-mentioned proteases, their roles in a living body, the relationship to the diseases, the clinical significance of these proteases inhibitors and the significance of the tests herein performed are explained below:

I. Trypsin: Trypsin is a protease existing originally in the form of proenzyme trypsinogen in the pancreas and the proenzyme is secreted into the small intestine where it is transformed into trypsin by activation with enterokinase existing therein. Trypsin has a role as one of digestive enzymes. If the trypsinogen is activated by any chance in the pancreas to form trypsin, the pancreas tissue will be injured to manifest clinically the symptoms of pancreatitis. In fact, it is known that in an experiment using rat as test animal, when trypsin is injected conversely into the pancreas, the onset of intense pancreatitis is observed but the disease is cured by the administration of a trypsin inhibitor. From this fact, it is presumable that the present compound having a strong trypsin inhibitory activity is useful as an antitrypsin agent which is clinically effective for the treatment of pancreatitis.

II. Plasmin: Plasmin is an enzyme existing in the blood, usually in the form of proenzyme plasminogen which is converted to plasmin by the activation with a plasminogen tissue activator such as urokinase. This enzyme acts reversely to the action of thrombin, that is, it acts to dissolve fibrin. For this reason, plasmin plays an important role in securing blood flow through capillaries. However, when this enzyme becomes abnormally activated for some reason, it causes hemorrhagic diseases. This enzyme participates also in inflammation, increasing the vascular permeability and causing edema or the like. Therefore, an inhibitor for this enzyme is useful as a drug to treat hemorrhagic diseases and inflammation.

III. Kallikrein: Kallikrein is an enzyme widely distributed in blood and other organs and glands, usually in the form of its precursor prekallikrein which is activated by Hageman factor or other proteases. This enzyme participates in the hypotensive kallikrein-kinin system which counteracts the hypertensive rein-angiotensin system and plays an important role in the control of blood pressure. This enzyme participates also in exogenous coagulation system. Further, kallikrein originated from organs or glands plays an important role in the improvement of local circulation. However, an abnormal activation, particularly an abnormal local activation, of this enzyme causes an insufficiently of local circulation due to the exaggeration of coagulation system, causing inflammation, ulcer, of the like. Therefore, a kallikrein inhibitor is useful for the control of blood pressure and as a drug for the treatment of inflammation or ulcer.

IV. Thrombin: Thrombin is known as an enzyme having a blood coagulating activity. In normal state, thrombin is formed by the activation of prothrombin in the blood when the vascular wall is injured. Thrombin acts to decompose the fibrinogen in the blood into fibrin. The resulting fibrin deposits on the injured part of vascular wall to prevent plasma components from transudation and simultaneously to promote the restoration of tissues. However, when the coagulation system is abnormally activated for some reason, a large number of fine thrombi are formed in capillaries throughout the entire body. Therefore, the present compound is useful as a drug for the treatment of such a disease.

MOST PREFERABLE EMBODIMENTS OF THE INVENTION

[Anti-trypsin, anti-plasmin, anti-kallikrein and anti-thrombin activities]

The anti-trypsin, anti-plasmin, anti-kallikrein and anti-thrombin activities were determined according to the method of Muramatsu et al. [M. Muramatsu, T. Onishi, S. Makino, Y. Hayashi and S. Fujii, J. of Biochem., 58, 214 (1965)]. The results were as shown in Table 1. The data summarized in Table 1 are expressed in terms of molar concentration ($ID_{50}$) of the test compound which inhibits 50% of the activity of each enzyme to hydrolyze TAME (tosylarginine methyl ester). The compound No. corresponds to the compound number shown in Examples. The figure in parentheses shows the percentage inhibition at a concentration of the compound of $1 \times 10^{-5}M$.

TABLE 1

| Compound No. | Trypsin | Plasmin | Kallikrein | Thrombin |
|---|---|---|---|---|
| 1 | $1 \times 10^{-5}$ | $8 \times 10^{-7}$ | $7 \times 10^{-7}$ | $9 \times 10^{-6}$ |
| 2 | $1 \times 10^{-6}$ | $2 \times 10^{-6}$ | $8 \times 10^{-7}$ | $3 \times 10^{-6}$ |
| 3 | $3 \times 10^{-7}$ | $1 \times 10^{-6}$ | $6 \times 10^{-7}$ | $8 \times 10^{-7}$ |
| 4 | $3 \times 10^{-6}$ | $1 \times 10^{-6}$ | $4 \times 10^{-7}$ | $2 \times 10^{-6}$ |
| 5 | $6 \times 10^{-6}$ | $1 \times 10^{-6}$ | $5 \times 10^{-7}$ | $2 \times 10^{-6}$ |
| 6 | $2 \times 10^{-6}$ | $3 \times 10^{-6}$ | $9 \times 10^{-7}$ | $2 \times 10^{-6}$ |
| 7 | $6 \times 10^{-7}$ | $5 \times 10^{-6}$ | $4 \times 10^{-6}$ | $6 \times 10^{-6}$ |
| 8 | $4 \times 10^{-6}$ | $3 \times 10^{-6}$ | $3 \times 10^{-6}$ | $6 \times 10^{-8}$ |
| 9 | $6 \times 10^{-6}$ | $2 \times 10^{-6}$ | $9 \times 10^{-7}$ | $6 \times 10^{-7}$ |
| 10 | $2 \times 10^{-6}$ | $5 \times 10^{-6}$ | $4 \times 10^{-7}$ | $6 \times 10^{-6}$ |
| 13 | $2 \times 10^{-6}$ | $5 \times 10^{-7}$ | $9 \times 10^{-7}$ | $1 \times 10^{-6}$ |
| 15 | $2 \times 10^{-6}$ | $2 \times 10^{-6}$ | $1 \times 10^{-6}$ | $1 \times 10^{-6}$ |
| 16 | $4 \times 10^{-6}$ | $9 \times 10^{-7}$ | $3 \times 10^{-6}$ | (49) |
| 18 | $2 \times 10^{-6}$ | $6 \times 10^{-7}$ | $2 \times 10^{-6}$ | $5 \times 10^{-6}$ |

The present compound and its pharmaceutically acceptable acid addition salts possess a strong C1 esterase (C1r̄, C1s̄) inhibitory activity, an ability of inhibiting the complement mediated hemolysis, and a therapeutic activity against the Forssman shock in which the activation of the complement system caused by an immune complex is said to play an important role. This indicates that the present compound is useful as an anti-complement agent effective for the treatment of allergic diseases such as nephritis associated with the complement.

The role of complement in the living body, the interrelation between a disease and the complement, the clinical significance of inhibitor, and the significance of tests (inhibition of C1r̄, C1s̄, complement mediated hemolysis, and Forssman shock) performed by the present inventors are described below.

Anti-complement activity:

(1) C1r̄, C1s̄

The complement is one of the serum components and comprises 9 components of C1 to C9. C1 is separated into 3 subcomponents of C1q, C1r and C1s. C1s̄ and C1r̄ mean activated C1s and activated C1r, respectively. The complement was thought at first to perform a part of the infection protective process of living body, since it shows bacteriolysis, but recently an intimate relation to the immunity has been evident. It was shown that the complement is activated by the immune complex progressively from C1 to C9 and exhibits cytolysis or hemolysis at the final stage (activation of C9). It was also disclosed that the fragments (e.g. C3a, C5a) liberated in the course of activation of the complement system exaggerate the vascular permeability and promote the chemotaxis of polymorphonuclear leucocytes or immune adherence. Since that time, the interrelationship between the abnormal activation of complement and various diseases, particularly immune diseases, has been extensively investigated and, as the result, the intimate association of autoimmune diseases with the complement is beginning to be disclosed. Examples of autoimmune diseases caused by the abnormal activation of complement include autoimmune hemolytic anemia, autoimmune thrombocytopenia, leukopenia, glomerulonephritis, systemic lupus erythematosus, serum sickness and periarteritis nodosa. It is expectable to cure such diseases by inhibiting the activation of complement or inhibiting the activated complement in an early stage. The present inventors examined the C1 esterase inhibitory effect of the present compound by using C1 esterase as target enzyme and, in addition, the influence of the present compound on the complement system to estimate the usefulness of the present compound as a drug for the treatment of autoimmune diseases.

(2) Complement mediated hemolysis:

The complement mediated hemolysis is widely used as a means to determine the titration of complement. The principle of this method is based on the fact that hemolysis is caused by the activation of complement, when the latter is added to a complex (immune complex) of erythrocytes and the antibody thereof. The degree of hemolysis varies in proportion to the amount of complement added. Therefore, when a known amount of complement admixed with a C1 esterase inhibitor is used, the hemolysis must be suppressed in proportion to the inhibitory activity. The present compound having C1 esterase inhibitory activity showed strong inhibition of complement mediated hemolysis as shown in Table 2.

(3) Forssman shock:

Quite different from other animals, guinea pig has on the surface of its organs a specific antigen called Forssman antigen which specifically reacts with the antibody of sheep erythrocyte. Forssman shock is based on the above principle and is a shock caused by the administration of antibody of sheep erythrocyte to a guinea pig. The Forssman shock was investigated in detail by many researches and it was definitely shown that this shock is a model case where the complement plays the principal part and that the shock is associated with a classical pathway in which the complement system is activated progressively starting from C1. Since the participation of complement in autoimmune diseases has been established, the Forssman shock can be said to be useful means for testing a drug for autoimmune diseases. A drug effective for the treatment of Forssman shock is useful as a drug of autoimmune diseases.

The present compounds are effective for the treatment of Forssman shock by oral administration, as shown in Table 3.

[Anti-complement activity]

(1) Anti-C1 (C1r̄, C1s̄) activity and inhibition of complement mediated hemolysis:

The anti-C1 esterase (C1r̄, C1s̄) activity was determined according to the method of Okamura et al. [K. Okamura, M. Muramatsu and B. Fujii, Biochem. Biophys. Acta, 295, 252–257 (1973)]. (2) The inhibition of complement mediated hemolysis was determined according to the method of Baker et al. [B. R. Baker and E. H. Erickson, J. Med. Chem., 12, 408–414 (1969)]. The results obtained were as shown in Table 2. The figures in Table 2 have the following meanings:

C1$\bar{\text{r}}$: Molar concentration of the test compound which inhibits 50% of the ability of C1$\bar{\text{r}}$ to hydrolyse AAME (acetylarginine methyl ester) (ID$_{50}$).

C1$\bar{\text{s}}$: Molar concentration of the test compound which inhibits 50% of the ability of C1$\bar{\text{s}}$ to hydrolyse ATEE (acetyltyrosin ethyl ester) (ID$_{50}$).

The figure in parentheses shows the percent inhibition at a concentration of the compound of $1 \times 10^{-5}$M. In hibition of complement mediated hemolysis (%):

The inhibitory activity is shown in terms of percent inhibition of the compound at varied concentrations.

Compound No.: The compound number shown in Examples

TABLE 2

| Compound No. | Anti-C1 activity C1$\bar{\text{r}}$ | C1$\bar{\text{s}}$ | Inhibition of complement mediated hemolysis (%) $1 \times 10^{-5}$ | $1 \times 10^{-6}$ | $1 \times 10^{-7}$ |
|---|---|---|---|---|---|
| 1 | (32) | $4 \times 10^{-7}$ | 97 | 70 | 6 |
| 2 | (35) | $7 \times 10^{-7}$ | 100 | 91 | 29 |
| 3 | (38) | $3 \times 10^{-7}$ | 93 | 25 | 0 |
| 4 | $1 \times 10^{-5}$ | $4 \times 10^{-7}$ | 100 | 96 | 48 |
| 5 | (41) | $3 \times 10^{-7}$ | 98 | 83 | 5 |
| 6 | $9 \times 10^{-6}$ | $4 \times 10^{-7}$ | 100 | 100 | 75 |
| 7 | $3 \times 10^{-6}$ | $3 \times 10^{-7}$ | 96 | 46 | 4 |
| 8 | (47) | $2 \times 10^{-6}$ | 100 | 93 | 34 |
| 9 | (41) | $4 \times 10^{-7}$ | 100 | 68 | 8 |
| 10 | (48) | $8 \times 10^{-7}$ | 100 | 86 | 20 |
| 11 | (24) | $2 \times 10^{-7}$ | 100 | 57 | 0 |
| 12 | (24) | $8 \times 10^{-8}$ | 100 | 59 | 0 |
| 13 | (46) | $5 \times 10^{-7}$ | 100 | 78 | 3 |
| 15 | $5 \times 10^{-6}$ | $9 \times 10^{-7}$ | 96 | 52 | 6 |
| 16 | (35) | $3 \times 10^{-6}$ | 100 | 89 | 25 |
| 18 | (37) | $2 \times 10^{-6}$ | 100 | 100 | 46 |

(3) Forssman shock:

The experiment was performed according to the method of I. G. Offerness et al. [Biochem. Pharmacol., 27 (14), 1873–1878 (1978)]. Male Hartley guinea pigs of about 350 g in body weight were used. Each guinea pig of the control group was administered intravenously with hemolysin (minimum dose to cause the shock) (commercial hemolysin, 5,000 U as assayed by the method of Ogata) and the time elapsed until death was observed. Each guinea pig of the treated group was administered intravenously with hemolysin after the animal was administered orally with compounds (100 mg/kg) and the time elapsed until death was observed.

TABLE 3

| Control group (sec.) | Group administered with compounds | |
|---|---|---|
| | Compound No. 1 | Compound No. 2 |
| 917 | Survival | Survival |
| 221 | 1291 | 1108 |
| 320 | 390 | Survival |
| 198 | 504 | 1255 |
| 715 | 613 | Survival |
| 627 | 404 | 980 |
| 354 | 868 | 855 |

Method of administration

The present compound is most suitably administered orally, though it can be administered intrarectally or by injection. It is used as a drug either alone or in combination with other drugs. It is administered generally in the form of medicinal composition, though it can be administered as simple substance without any additive. Examples of medicinal composition include tablets, powders, capsules, syrups and solutions. An oral composition may contain common additives such as binders, diluents, lubricants, disintegrators and excipients. Oral solutions may be in the form of aqueous or oily suspension, solution, emulsion, syrup or elixir, or in the form of dry syrup which, before use, is readjusted with water or other suitable solvents. The solutions may contain common additives such as suspending agents, flavoring agents, diluents, or emulsifiers. For injection, there may be used aqueous suspensions or oily suspensions.

Dosage

The present compound may be administered to mammals (including man) orally at a dose of 10 to 200 mg per day or by intravenous injection at a dose of 1 to 20 mg per day. However, these doses are presented solely for the sake of example. A suitable dose for a patient should be determined depending upon the age and body weight of the patient and the features of illness.

Examples of pharmaceutical formulations are described below.

Examples of pharmaceutical formulations:

| (1) Capsules: | |
|---|---|
| The present compound | 100.0 mg |
| Lactose | 59.0 |
| Crystalline cellulose | 33.4 |
| Calcium carboxymethylcellulose | 3.6 |
| Magnesium stearate | 4.0 |
| Total | 200.0 mg |
| (2) Fine granules: | |
| The present compound | 50.0 mg |
| Lactose | 249.0 |
| Mannitol | 75.0 |
| Corn starch | 110.0 |
| Hydroxypropylcellulose | 16.0 |
| Total | 500.0 mg |
| (3) Injections: | |
| The present compound | 5.0 mg |
| Water for injection | 2 ml |

Made up to injections in a customary manner.

Toxicity

The median lethal dose (LD$_{50}$) of the present compound is as shown in Table 4.

TABLE 4

| | LD$_{50}$ mg/kg (mouse) | |
|---|---|---|
| Compound No. | I.V. | P.O. |
| 2 | 19 | >3000 |

The hereinafter set out examples are intended to illustrate the production of the present compounds and not limit it in spirit or scope.

TABLE 5

$$\begin{array}{c} R_1-N \\ \phantom{R_2}\diagdown \\ R_2 \\ \phantom{R_2}\diagup \\ R_3 \end{array}$$

| Compound No. | Structure | Salt | mp °C. | IR$\nu_{max}^{KBr}$ cm$^{-1}$ (—COO—) |
|---|---|---|---|---|
| 1 | H₃C—N, H₃C—HN (with =) | HCl.MSA / 2MSA | 269–271 / 271–274 | |
| 2 | imidazolidine (NH, NH, =) | 2HCl / 2MSA | 274–277 (d) / 242–244 (d) | |
| 3 | imidazolidine (NH, N-CH₃, =) | 2MSA | 240–242 | |
| 4 | 4-methyl imidazolidine (NH, NH, =) | 2MSA | 198–204 | |
| 5 | tetrahydropyrimidine (NH, NH, =) | 2MSA | 240–242 | |
| 6 | hexahydrobenzimidazole (NH, NH, =) | 2HCl | 188 (d) | |
| 7 | imidazole (N, NH) | 2HCl | 288–290 (d) | |
| 8 | HN=, H₃C—HN | 2HCl | 255–259 (d) | |
| 9 | HN=, H₃C—N(CH₃) | 2MSA | 241–243 (d) | |
| 10 | HN=, H₅C₂—HN | 2MSA | 238–242 | |
| 11 | H₃C—N=, H₅C₂—HN | HCl.MSA | | 1730 |

TABLE 5-continued

| Compound No. | $R_1-N\!\!=\!\!\underset{R_3}{\overset{R_2}{N}}\!\!-\!$ | Salt | mp °C. | IR$\nu_{max}^{KBr}$ cm$^{-1}$ (—COO—) |
|---|---|---|---|---|
| 12 | $H_5C_2-N\!\!=$ <br> $H_5C_2-HN$ | HCl.MSA | | 1730 |
| 13 | $HN\!\!=$ <br> $H_3C-(CH_2)_3-HN$ | 2MSA | 240–243 | |
| 14 | $H_3C-N\!\!=$ <br> $H_3C-(CH_2)_3-HN$ | 2HCl | | 1720 |
| 15 | $HN\!\!=$ <br> $HO-(CH_2)_2-HN$ | 2HCl | 205–208 (d) | |
| 16 | $HN\!\!=$ <br> $H_3CCONH-(CH_2)_2-HN$ | 2HCl | | 1725 |
| 17 | $HN\!\!=$ <br> $C_{15}H_{31}COO-(CH_2)_2-HN$ | 2$C_{15}H_{31}$COOH | 105–109 (d) | |
| 18 | $HN\!\!=$ <br> Ph-$CH_2-O-(CH_2)_2-HN$ | 2HCl | 136–140 (d) | |

MSA shows methanesulfonate.
"d" in parenthesis means decomposition.

EXAMPLE 1

(Compound No. 1)

Synthesis of 6-amidino-2-naphthyl 4-(2,3-dimethyl)guanidino-benzoate

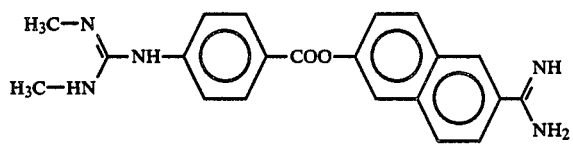

To 7.9 g of 4-(2,3-dimethyl)guanidinobenzoic acid hydrochloride, 8.24 g of 6-amidino-2-naphthol methanesulfonate and 10 g of DCC was added 25 ml of anhydrous pyridine and the resulting mixture was stirred overnight at room temperature. To the mixture was added 200 ml of acetone. The precipitate which was formed was collected by filtration. To the precipitate was added 30 ml of water. The insolubles were removed by filtration. The filtrate was distilled under reduced pressure and 200 ml of acetone was added to the residue. The precipitate which was formed was collected by filtration. The precipitate was suspended in 30 ml of DMF, stirred and 3.1 g of methanesulfonic acid was added to the suspension. To the resulting mixture was added 200 ml of ether and the solvent was removed by decantation. To the residue was added 60 ml of ethanol and the mixture was stirred. The precipitate was collected by filtration to obtain 10.31 g of 6-amidino-2-naphthyl 4-(2,3-dimethyl)guanidino-benzoate dimethanesulfonate.

Alternatively, to 1 g of 4-(2,3-dimethyl)guanidinobenzoic acid hydrochloride, 1.16 g of 6-amidino-2-naphthol methanesulfonate and 1.27 g of DCC was added 3 ml of anhydrous pyridine and the resulting reaction mixture was treated as described above to yield 0.96 g of 6-amidino-2-naphthyl 4-(2,3-dimethyl)-guanidino-benzoate hydrochloride methanesulfonate.

EXAMPLE 2

(Compound No. 2)

Synthesis of 6-amidino-2-naphthyl 4-(2-imidazolinyl)amino-benzoate

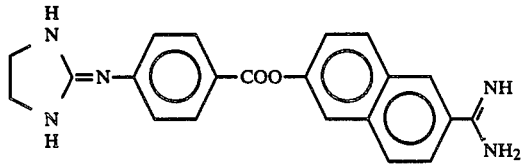

To 1.03 g of 4-(2-imidazolinyl)amino-benzoic acid methanesulfonate, 0.96 g of 6-amidino-2-naphthol methanesulfonate, 42 mg of DMAP and 1.06 g of DCC was added 5 ml of anhydrous pyridine. The resulting mixture was stirred overnight at room temperature. To the mixture was added 50 ml of acetone and the precipitate which was formed was collected by filtration. To the precipitate was added 40 ml of DMF. After stirring the precipitate which was formed was collected by filtration and 20 ml of water was added to the precipitate. The insolubles were removed by filtration. The filtrate was distilled under reduced pressure. To the residue was added 200 ml of acetone. The precipitate which was formed was collected by filtration to obtain 0.8 g of 6-amidino-2-naphthyl 4-(2-imidazolinyl)amino-benzoate dimethanesulfonate.

Alternatively, 4 g of 4-(2-imidazolinyl)amino-benzoic acid hydrochloride, 4.67 g of 6-amidino-2-naphthol methanesulfonate and 0.2 g of DMAP were dissolved in 60 ml of anhydrous pyridine, 5.13 g of DCC was added to the solution and then the reaction mixture was treated as described above, via a carbonate salt, to yield 2.35 g of 6-amidino-2-naphthyl 4-(2-imidazolinyl)amino-benzoate dihydrochloride.

Compounds Nos. 3 to 18 were obtained as in Examples 1 and 2.

POSSIBILITY OF INDUSTRIAL USE

The present amidine compounds are of use as anti-trypsin, anti-plasmin, anti-kallikrein, anti-thrombin and anti-complement agents which may be administered orally.

We claim:

1. Compound of formula (I)

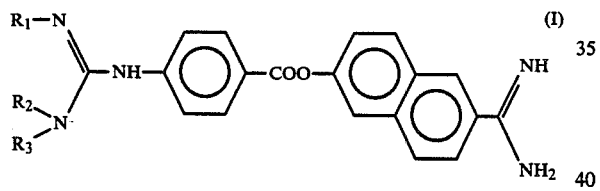

wherein
   $R_2$ represents a hydrogen atom or a straight or branched chain alkyl group of 1 to 6 carbon atoms; and
   $R_1$ and $R_3$ taken together form a straight alkylene alkenylene chain of 2 to 4 carbon atoms that may be optionally substituted by one or more straight or branched chain alkyl groups of 1 to 4 carbon atoms, or $R_1$, $R_2$ and $R_3$ taken together with the nitrogen atoms with which they are bonded form 4,5-cyclohexanoimidazoline;
   or a pharmaceutically acceptable acid addition salt thereof.

2. Compound according to claim 1, wherein the group

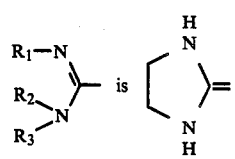

or a pharmaceutically acceptable acid addition salt thereof.

3. Compound according to claim 1, wherein the group

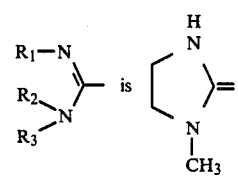

or a pharmaceutically acceptable acid addition salt thereof.

4. Compound according to claim 1, wherein the group

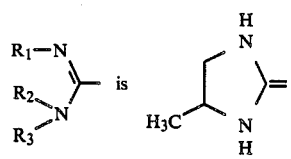

or a pharmaceutically acceptable acid addition salt thereof.

5. Compound according to claim 1, wherein the group

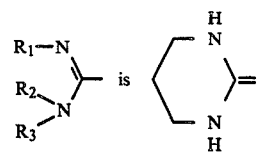

or a pharmaceutically acceptable acid addition salt thereof.

6. Compound according to claim 1, wherein the group

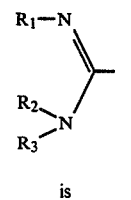

is

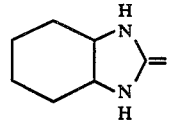

or a pharmaceutically acceptable acid addition salt thereof.

7. Compound according to claim 1, wherein the group

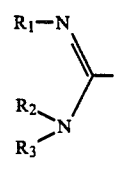

is

-continued

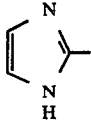

or a pharmaceutically acceptable acid addition salt thereof.

8. Compound of formula (I)

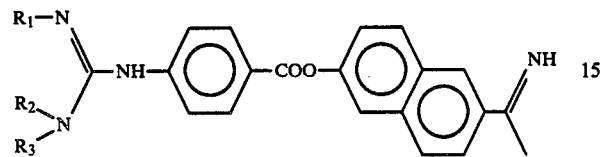

wherein
R₁ and R₂ each represent a hydrogen atom;
R₃ represents a group of the formula R₄—B—(CH₂-)$_n$— wherein
n is 1 to 2,
B is —O— or —NH— and
R₄ is a hydrogen atom, R₅—CO— or

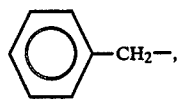

and
R₅ is a straight or branched chain alkyl group of 1 to 15 carbon atoms;
or a pharmaceutically acceptable acid addition salt thereof.

9. Compound according to claim 8, wherein the group

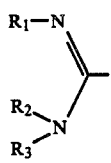

is

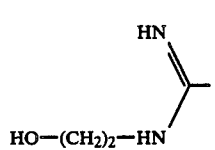

or a pharmaceutically acceptable acid addition salt thereof.

10. Compound according to claim 8, wherein the group

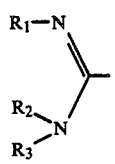

-continued
is

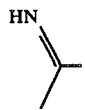

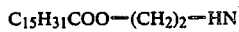

or a pharmaceutically acceptable acid addition salt thereof.

11. Compound according to claim 8, wherein the group

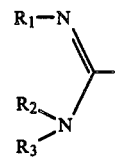

is

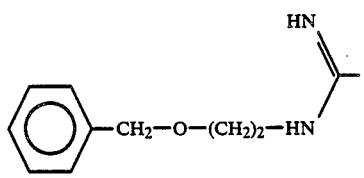

or a pharmaceutically acceptable acid addition salt thereof.

12. Compound of formula (I)

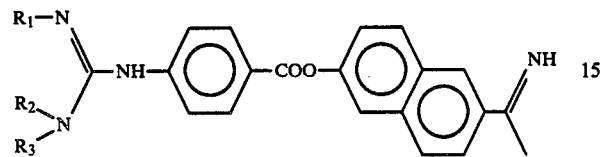

wherein
R₁ and R₂ each represent a hydrogen atom;
R₃ represents a group of the formula R₄—B—(CH₂-)$_n$— wherein
n is 1 to 2,
B is —NH— and
R₄ is R₅—CO—, where R₅ is a straight or branched chain alkyl group of 1 to 15 carbon atoms;
or a pharmaceutically acceptable acid addition salt thereof.

13. Compound according to claim 12, wherein the group

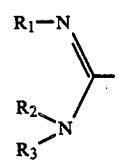

is

-continued

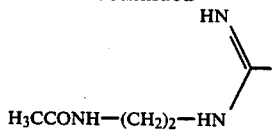

or a pharmaceutically acceptable acid addition salt thereof.

14. Compound of formula (I)

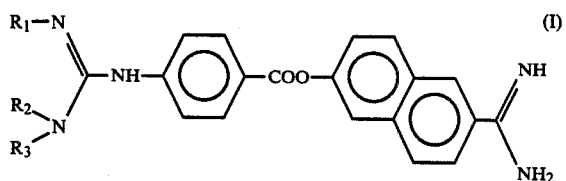

wherein
  $R_1$ and $R_2$ represents each a hydrogen atom, or a straight or branched chain alkyl group of 1 to 6 carbon atoms;
  $R_3$ represents a straight or branched chain alkyl group of 1 to 6 carbon atoms, or a group of the formula $R_4$—B—$(CH_2)_n$— wherein n is 1 to 2;
  B is —O— or —NH— and
  $R_4$ is a hydrogen atom, $R_5$—CO— or

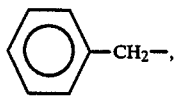

$R_5$ is a straight or branched chain alkyl group of 1 to 15 carbon atoms; and
  wherein when $R_1$ and $R_2$ represents each a hydrogen atom, then $R_3$ represents the group of the formula $R_4$—B—$(CH_2)_n$—; and
  wherein when $R_2$ represents a hydrogen atom or a straight or branched chain alkyl group of 1 to 6 carbon atoms, then $R_1$ and $R_3$ taken together form a straight alkylene or alkenylene chain of 2 to 4 carbon atoms that may be optionally substituted by one or more straight or branched chain alkyl groups of 1 to 4 carbon atoms, or $R_1$, $R_2$ and $R_3$ taken together with the nitrogen atoms with which they are bonded form 4,5-cyclohexanoimidazoline;
  or a pharmaceutically acceptable acid addition salt thereof.

15. Product represented by the structural formula:

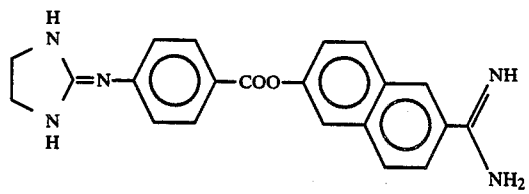

or a pharmaceutically acceptable addition salt thereof.

16. Product produced by reacting 4-(2-imidazolinyl)-amino-benzoic acid methanesulfonate and 6-amidino-2-naphthol methanesulfonate, in the presence of an organic solvent to obtain a reaction mixture containing 6-amidino-2-naphthyl 4-(2-imidazolinyl)-amino-benzoate dimethanesulfonate.

17. A pharmaceutical composition having anti-trypsin, anti-plasmin, anti-kallikrein, anti-thrombin and anti-complement activities and which may be administered orally comprising a therapeutically effective amount of a compound of the formula

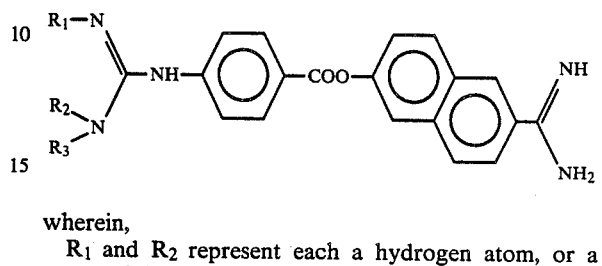

wherein,
  $R_1$ and $R_2$ represent each a hydrogen atom, or a straight or branched chain alkyl group of 1 to 6 carbon atoms;
  $R_3$ represents a straight or branched chain alkyl group of 1 to 6 carbon atoms, or a group of the formula $R_4$—B—$(CH_2)_n$— wherein n is 1 to 2;
  B is —O— or —NH— and
  $R_4$ is a hydrogen atom, $R_5$—CO— or

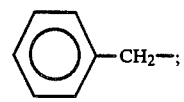

$R_5$ is a straight or branched chain alkyl group of 1 to 15 carbon atoms; and
  wherein when $R_1$ and $R_2$ represent each a hydrogen atom, then $R_3$ represents the group of the formula $R_4$—B—$(CH_2)_n$; and
  wherein when $R_2$ is hydrogen or a straight or branched chain alkyl group of 1 to 6 carbon atoms, then $R_1$ and $R_3$ taken together form a straight alkylene or alkenylene chain of 2 to 4 carbon atoms that may be optionally substituted by one or more straight or branched chain alkyl groups of 1 to 4 carbon atoms; or $R_1$, $R_2$ and $R_3$ taken together with the nitrogen atoms with which they are bonded form 4,5-cyclohexanoimidazoline;
  or a pharmaceutically acceptable acid addition salt thereof, or mixtures thereof, and a pharmaceutically acceptable carrier therefor.

18. A pharmaceutical composition having anti-trypsin, anti-plasmin, anti-kallikrein, anti-thrombin and anti-complement activities and which may be administered orally comprising a therapeutically effective amount of the compound

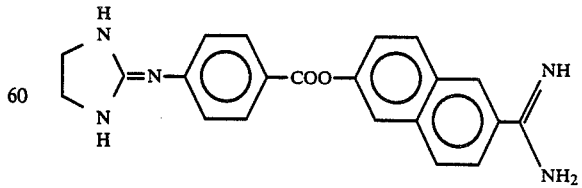

or a pharmaceutically acceptable acid addition salt thereof and a pharmaceutically acceptable carrier therefor.

* * * * *